United States Patent [19]

Leva

[11] 3,933,953
[45] Jan. 20, 1976

[54] APPARATUS FOR DEODORIZING FATS AND OILS

[76] Inventor: Max Leva, 5118 Hayes St., Hollywood, Fla. 33021

[22] Filed: June 6, 1972

[21] Appl. No.: 260,209

[52] U.S. Cl. .............. 261/148; 261/113; 261/152; 426/488; 159/15; 55/54
[51] Int. Cl.² ........................................ B01D 3/22
[58] Field of Search .............. 260/428; 203/96, 73; 202/153, 158; 261/148, 113, 152

[56] References Cited
UNITED STATES PATENTS

| | | | |
|---|---|---|---|
| 1,743,131 | 1/1930 | Grace | 260/428 |
| 2,224,925 | 12/1940 | Potts | 203/96 |
| 2,224,986 | 1/1940 | Potts | 203/96 |
| 2,224,986 | 12/1940 | Potts | 203/87 |
| 2,368,669 | 2/1945 | Lee | 260/428 |
| 2,377,781 | 6/1945 | Hebbard | 261/148 |
| 2,422,185 | 6/1947 | Dean | 260/428 |
| 2,664,391 | 12/1953 | Coulter | 203/78 |
| 2,804,427 | 8/1957 | Suriano | 260/428 |
| 3,075,752 | 1/1963 | Leva | 261/113 |
| 3,367,638 | 2/1968 | Leva | 261/113 |

OTHER PUBLICATIONS

Webster's New World Dictionary, World Pub. Co., N.Y. 1968, pp. 254, 917.

Primary Examiner—Norman Yudkoff
Assistant Examiner—Hiram H. Bernstein
Attorney, Agent, or Firm—William J. Ruano

[57] ABSTRACT

Apparatus and method for stripping fatty acids and removing objectionable odors or flavors from oils and fats comprising a chamber which encloses a stack of horizontal, parallel disposed plates, each plate having a plurality of apertures defined by chimneys and extending downwardly from the plates. Thin films of heated oil collect on the plates while superheated steam is passed upwardly through said chimneys and over said films to boil out fatty acids and volatile, odor-forming matter. Preferably a separate oil-sealed lower compartment is provided for cooling the oil, stripped and deodorized, which enters through traps into a sealed lower section before the oil is removed from the chamber. It is also preferable to pass heated oil, before introduction into said chamber, through a preliminary flash chamber of similar construction to said chamber. Inert gas, such as nitrogen or steam, is passed upwardly of the chimneys to strip fatty acids from the films of oil.

9 Claims, 2 Drawing Figures

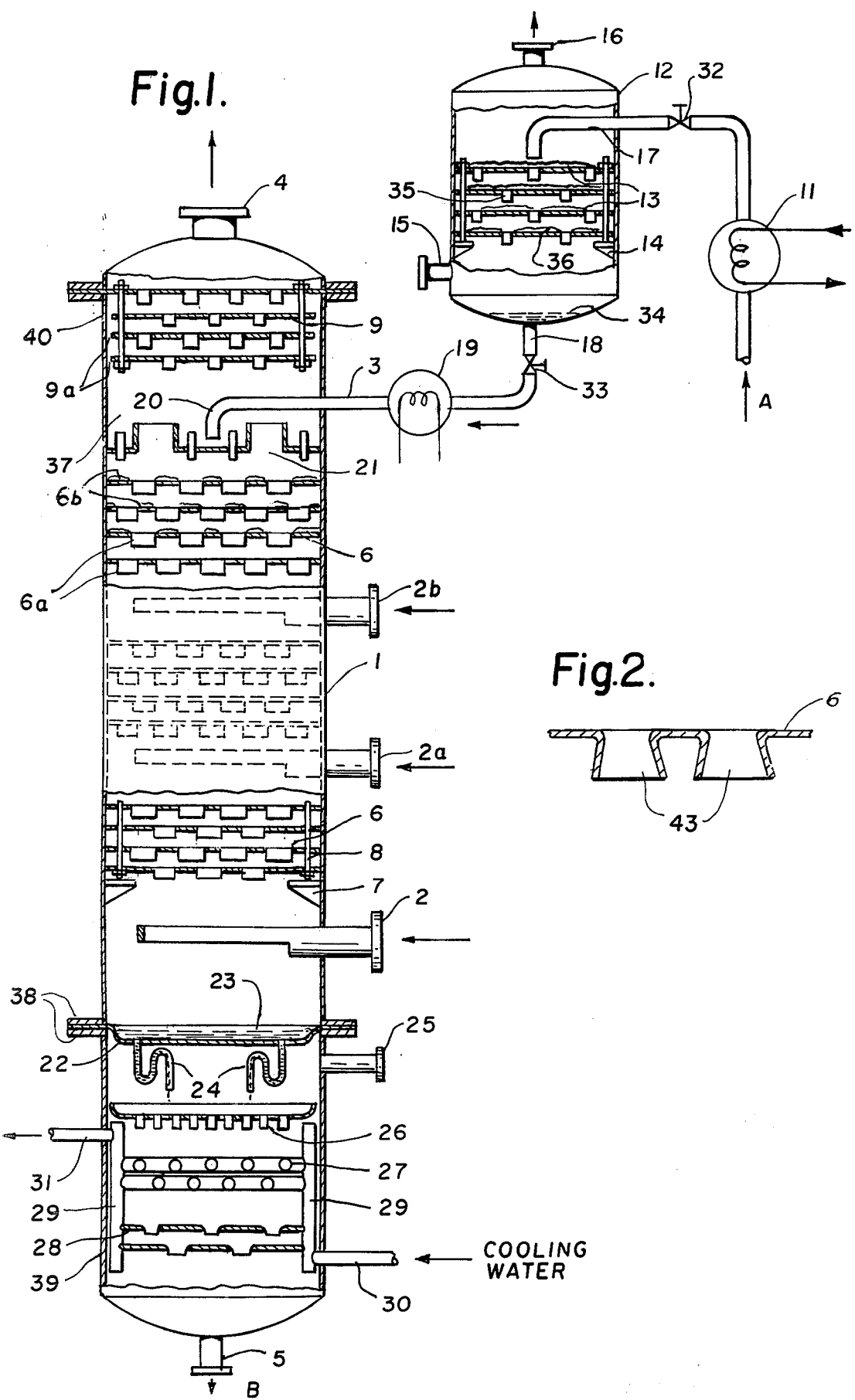

APPARATUS FOR DEODORIZING FATS AND OILS

This invention pertains to apparatus and a method for refining edible oils and fats and particularly for removing objectionable odors or flavors from oils and fats and fatty acids and gylcerine. These oils and fats may either be of vegetable origin, such as soybean oil, peanut oil sunflower oil, palmoil, etc. just to mention a few, or they may be of animal origin, such as, for instance, fish oils, tallow or lard. Depending on the normal temperature of usage of these materials, they may either be liquid or semi-solid. Generally, speaking, these oils and fats are principally composed of glyceryl esters of fatty acids, which may either be saturated or unsaturated as far as their chemical bondings is concerned. The following discussion is about oils, however, it should be understood that this includes fats as well.

After the general processing of these oils in the course of their manufacture, they will usually contain greater or lesser amounts of free fatty acid, as well as other volatile odoriferous and flavorous materials, which are generally very distinct and are the cause of the objectionable odor of these oils. In their undeodorized state, these oils are, therefore, not readily palatable for food purposes and their odors and tastes must be improved.

Generally speaking, the objectionable odoriferous materials are quite volatile when compared to the usually much less volatile character of the oils in which they are found, and it is this particular property which permits the removal of the odoriferous substances from the oils by a relatively simple step of stripping these oils with a gas or vapor. Frequently, the stripping agent may be steam and the operation is then better known as steam distillation. When, therefore, in the following discussion reference is merely being made to steam as the stripping agent, it is understood that thereby other inert agents, such as, for instance, nitrogen gas or other gases are not excluded and may, under the proper conditions of temperature and pressure, be used as well.

The actual deodorization is most frequently achieved by contacting the oils with open steam at elevated temperatures and sub-atmospheric pressures. Depending on the operating pressure, these temperatures may range from about 300°F., at very low pressures, to perhaps 550°F. at higher pressures.

Under normal circumstances, the oils will contain greater or lesser amounts of dissolved oxygen. Thus, a typical oil to be deodorized may initially contain from 2 to 3 percent of oxygen, by volume, at ordinary room temperature of 60°F. and under atmospheric pressure. If an oil with such an oxygen content is subjected to the temperatures that are normally required for deodorization with steam, the oil may suffer great damage as far as color and composition is concerned. Hence, it is necessary that oils of high oxygen content be first deaerated before they are deodorized. It is, therefore, the general practice to reduce the oxygen content in the oil well below 0.1 percent, by volume, and preferably below 0.05 percent, by volume, before the oil is deodorized. The deaeration step is generally accomplished by subjecting the oil to a temperature of about 175°–250°F. and applying a moderate vacuum of say 5 to 100 millimeter of mercury. Frequently an inert vapor, such as steam, may be injected into the hot oil (up to 0.25 percent of the oil) which acts as a purge for the release of oxygen.

After the oil has been properly deodorized, it must be cooled before it can be exposed to air, as otherwise renewed degeneration of the oil will set in. For most oils, the final temperature before handling and packaging should preferably be less than 150°F. It is extremely important that during the oil cooling process all air contact is avoided.

The most frequently used equipment for the abovementioned three steps were vertically arranged confining vessels into which were suspended relatively deep tanks, in such a manner that an annular free area was around each tank and the vessel wall. The tanks were arranged vertically above each other and connected by piping for the downward transport of the oil. A typical unit of this type may have contained as many as four, five or more such vertically arranged tanks, and the entire confining vessel was evacuated down to a very low operating pressure of perhaps a few millimeters of mercury or even less. The upper one or two tanks were fitted with closed heating coils, using either steam, dowtherm or some other heating medium, and the oil entered the top tank and was heated to the proper deaeration temperature by the closed heating coils. In order to achieve the release of the dissolved air, a very high retention time of usually much more than an hour was required. After the proper deaeration, the oil would enter the second tank where its temperature would be increased to near the deodorization temperature. This was accomplished after a similarly high retention time as used in the deaeration step and the oil would flow further down to successive tanks, fitted with open spargers where steam would enter the charge and drive the odoriferous materials out of the oil. The steam now carrying the odoriferous material escaped through the annular passageway into the vacuum system and out. For proper deodorization and depending on the oil in question, several such deodorization tanks in series may be required. Finally, the deodorized oil would flow into a final tank in which would be submerged cooling coils for properly chilling the deodorized oil to a safe discharge temperature.

The system just described has the very serious disadvantage of requiring for its operation a very large holdup of oil, and hence a very long contact time is required. Moreover, due to generally deep layers of oil processed in each stage, the contacting efficiencies are very poor, and the cost of equipment material required per unit weight of oil processed is very unsatisfactory. This is especially so since in this type of operation, expensive stainless steels and similar metals are required. Finally, with the very high hold-ups, the equipment is not satisfactory to permit readily changeovers to different oils and unusually awkward and time consuming cleaning cycles are required if product contamination is to be reduced to an acceptable level.

In order to attempt to overcome the inherent difficulties of the equipment, just discussed, vertical towers have been proposed which were equipped with the usual type of contacting plates, such as of the bubble cap, sieve or valve type. It is well known that in these plates the relative liquid and vapor flow is such that the vapor must bubble through a relatively deep liquid layer in order to make contact with the liquid. Since the liquid viscosities of the oils processed are normally quite high and since the type of plates considered here are notoriously ineffective gas-liquid contactors when viscous liquids are involved, it has been found that the poor contact efficiencies had to be compensated for by additional large auxiliary liquid hold zones. Hence, the total hold-up of the equipment was not much improved over that of the abovementioned vertical tank units.

A further attempt at reducing the liquid hold-up and the resulting processing time and consequently improved process flexibility was attempted by proposing equipment that uses tubular equipment that employs vertical falling films or packings. Vertical films are notorious for their instability of operation, lack of homogeneity of thickness and sensitivity to deposits of impurities on the surfaces carrying the films. Vertical liquid films along tubes have for these reasons, therefore, not found any widespread usage in oil deodorization by themselves, and still large hold-up areas are required to compensate for the low contacting efficiencies. Packings contained in towers may perhaps provide more reliable vertical contacting if the packing can be effectively wetted. But here again the relatively high liquid viscosity makes effective wetting nearly impossible. This results then in poor contacting efficiencies which must be compensated for by using very great packed tower heights. Thus, for ordinary oil deodorizations and using the usual conventional tower packings, such as say 1-inch Pall rings, for example, packed heights of 20 feet or more are required. This will lead to very large liquid hold-ups again and all the disadvantages that are inherent with the units so far mentioned.

Now besides deaeration and deodorization, oil and fat refining also involves the removal of appreciable amounts of free fatty acids that occur in an oil or fat in the course of its general processings. Reference is being made to appreciable amounts of free fatty acid, namely, quantities of several percent, by weight, of the neutral oil or fat that may be contained, — in other words, quantities that may range from a percent or two to perhaps 10 percent. Most frequently, these free fatty acids have, in the past, been recovered from the oils or fats by washing the acid oil with a weak solution of caustic soda, thus forming a sodium soap in solution, that is then separated from the oil, and the oil must then be refined further. This caustic washing while, of course, serviceable for removing the free fatty acid, is very awkward, hence special distillation methods which are mostly steam stripping processes have been proposed using the conventional packings and types of plates of bubble cap, sieve and valve construction for removing the free fatty acids from the neutral oil.

An object of the present invention is to overcome the abovementioned disadvantages of conventional apparatus and methods for deodorization and fatty acid stripping by providing very low liquid hold-up and low pressure drops, features which are particularly well suited to save on process steam, when compared with the conventional methods of distillation, using the variously known common contacting plates and tower packings.

Another aspect of oil and fat refining involves the removal of free glycerine from the neutral glycerides. Just as the removal of free fatty acid from a neutral fat or oil, this operation also uses open steam as a diluent, which contacts the oil or fat containing the free glycerine. Normally the amounts of glycerine which are in such oils or fats are of the order of magnitude of 3 to 10 percent and removal to less than 0.1 percent is generally desirable.

Another object of the invention is to provide a novel apparatus and method for handling these steam carried glycerine distillations as effectively as it does the fatty acid separations, where open steam is used as well as diluent and temperature depressant. When, therefore, in the following description, reference data are merely given for the new equipment and how it handles free fatty acid removal it is tactily understood that this information also applies especially well to the case where free glycerine is to be separated from neutral oils or fats.

All these aforementioned operations where oils or fats are being contacted by steam, which is usually superheated, are here referred to as steamrefining of the oils or fats.

Other objects and advantages will become more apparent from a study of the following description, taken with the accompanying drawing wherein:

FIG. 1 is an elevational view, with parts shown broken away and others illustrated somewhat schematically, illustrating apparatus, embodying the present invention for removing objectionable odors or flavors as well as fatty acid and glycerine from oils and fats; and, FIG. 2 is a fragmentary, cross-sectional view of a modification of the depending chimneys.

In accordance with the invention, it has now been found, quite unexpectedly, that by using plates that will generate a horizontal film flow through the tower, the liquid hold-up may be drastically reduced and, at the same time, the efficiency of contacting is maintained at such a very high level that for contact times of generally less than a minute, the height of the contacting zone may be drastically shortened over that of the other units discussed. The type of plate equipment to which reference is made is described in detail in U.S. Pat. Nos. 3,075,752 and 3,367,638. The plates present perfectly flat, unobstructed horizontal surfaces from which short chimneys depend downwardly.

Reference is made to FIG. 1 of the drawing which shows a system for removing oils and fats and embodying the principles of the present invention.

The raw oil is pumped into the system at A and passed through heater 11 where its temperature is raised to about 175° to 250°F. The flow rate of the oil is controlled by valve 32. The oil enters then, through pipe 17, into flash chamber 12. The top 16 of the chamber is connected to a reduced pressure zone and the pressure maintained in the chamber may vary from about 5 to perhaps 100 mm Hg., or more.

Up to now the practice has been to permit the oil to expand into the low pressure chamber by carefully controlling valve 32. In the course of this expansion, the dissolved oxygen is generally given off and drawn off through the pipe 16 by the vacuum. The disadvantages of such an expansion process into a partially evacuated vessel are, however, firstly, substantial oil mist is formed and is lost through 16 into the vacuum system, and secondly the partly deaerated oil cannot be purged by an inert gas. In order to attempt to minimize the mist loss and permit simultaneous purging, packings have, on occasion, been suggested inside the flash chamber 12. However, with packings the hold-up in the flash chamber is very much increased and the rate of oxygen release correspondingly retarded.

It has now been found, unexpectedly, that if flash chamber 12 is fitted with horizontal flat plates 13, as described in earlier U.S. Pat. Nos. 3,075,752, and 3,367,638, the plates being supported on lugs 14, and equipped with depending short chimneys 35, and if the oil coming from pipe 17 is allowed to impinge on the uppermost plate of such a stack, the oil will form a thin film 36 across the plates and the oil will move on downwardly. At the same time an inert purge gas, such as nitrogen, steam or other inerts, may be admitted into the bottom inlet pipe 15 of the flash chamber and in its travel upwardly through the chimneys 35 and over the liquid film 36 will sweep the released oxygen upwardly and out into the vacuum system.

With the aid of such a flash chamber 12, when fitted with the horizontal plates 13, it is thus found that the release of the dissolved oxygen is much more complete than when ordinary packings are used over which the oil drops randomly and forms relatively thick streams. The amounts of inert gas, such as nitrogen or superheated steam, that may be introduced at 15 may vary from about 0.1 to 1.0 percent of the weight of the oil, and preferably from 0.25 to 0.50 percent of the oil. The original oxygen content of an oil that enters the flash chamber 12 may be about 2 to 3 percent, by volume, of the oil and the deaerated oil leaving through 18 will normally contain of the order of magnitude of 0.1 percent, by volume, or less of oxygen. The horizontal plates 13 in the chamber 12 may be spaced between 0.25 to 6 inches apart, the preferred distance being 0.50 to 3 inches. The diameter of the depending chimneys 35 may vary similarly from 0.25 to 4 inches, — the preferred diameter being, however, between 0.5 and 2 inches. As will be seen from FIG. 1, the chimneys 35 in the plates 13 are spaced relatively far apart. Thus if the diameter of the chimneys 35 is denoted by $d$, the distance between the centers of two adjoining chimneys in these plates should generally be larger than $2d$ for best results. The number of horizontal trays that are usually required for effective release of the dissolved oxygen are relatively few in number, say between 3 and 12, and the resulting liquid hold-up on these plates is virtually negligible.

After effective deaeration, valve 33 is manipulated and the now deaerated oil leaves the flash chamber 12 through pipe 18. The oil now enters heater 19 where its temperature is raised to about 370° to 550°F.. From the heater the oil passes through pipe 3 into the deodorization chamber 1. The deodorization chamber is generally under a considerably lower pressure than the flash chamber 12. Hence, for transporting the oil to chamber 1, it suffices, therefore, to merely manipulate carefully valve 33 to permit the oil to flow into chamber 1. In order to make sure that none of the gaseous deaeration products released in flash chamber 12 are sucked into the deodorization chamber 1, it is recommended that a slight liquid level 34 be always maintained in flash chamber 12. This is very simply achieved by permitting valve 33 to be actuated by the liquid level 34 in the flash chamber 12 by some sort of liquid level control mechanism (not shown in FIG. 1), of which there are many suitable kinds in the equipment market.

As will be seen, the deodorization chamber 1 consists essentially of two separate sections. The upper section 37, in which the deodorization proper takes place, is above flanges 38. Below flanges 38 there is a lower section 39 which serves merely the purpose of cooling the deodorized oil. Both sections are separated from each other by separating membrane 22, the function of which will be discussed later.

The upper section of the deodorization chamber 1 is fitted with horizontal contact plates 6, generally in accord with the disclosures in the abovementioned U.S. patents. These plates are arranged in close proximity to each other and are mounted on lugs 7 by means of rods 8 that pass through the stacks and hold the plates properly spaced together. In actual practice, usually between 5 to perhaps as many as 50 horizontal plates may be assembled in one stack, though the generally preferred number per stack ranges from 15 to 35. The plate spacing varies from about 0.25 to 6 inches and the preferred distance is between 0.75 to 3 inches. It is preferred that the depending chimneys 43 should be conically shaped, as shown in FIG. 2, with the wide part pointing downwardly but they may also be straight, cylindrical, short pieces, or of other shapes. The lengths of the chimneys will vary between about ⅛ inch to about 3 inches with ¼ to 1½ inches long preferred.

As will be seen from FIG. 1, in contrast to the horizontal plates 13 in the flash chamber 12, the chimneys 6a, depending from the plates 6 in the deodorization chamber 1, are spaced relatively closely together. Thus if we designate the average diameter of a chimney by $d$ it has been found that for best deodorization as well as fatty acid removal, the distance between the centers of adjacent chimneys should preferably be less than $2d$. It has been found further that for deodorization as well as stripping of fatty acids and glycerine, the diameter of the chimneys should not be smaller than 0.5 inch and not larger than 4 inches for best results.

In all instances it is, however, quite essential from the point of view of cleanliness that these chimneys 6a be made in one single piece, preferably by stamping out from metal strip. In this way there will be no welded seam in the chimneys. Since the material to be processed on these plates are primarily foods which are wholly organic matter, they are very prone to deterioration by bacteria. The utter absence of any welds will therefore enhance the ease of keeping the equipment clean and sanitary. Furthermore, the chimneys 6a are expanded tightly into a carefully extruded orifice hole with no welding around the perimeter of the chimneys, so that the equipment will drain clean with the least liquid flows and prevent contaminations.

The oil coming from the flash chamber 12 through heater 19, pipe 3 and delivery elbow 20, as already described, enters the deodorization chamber 1 by emptying on top of a liquid distributor 21. This can be any kind of suitable liquid distributor, — however the kind described in U.S. Pat. No. 3,446,489, is preferred. From the liquid distributor the oil empties on the horizontal plate stacks below. As the oil flows through the plate stacks, it does so by forming a multitude of very thin continuous films 6b across the horizontal plates. The order of magnitude of the thickness of these films is between 0.25 to perhaps 2 millimeters, depending somewhat on the oil flow rates as well as the viscosity of the oil under operating conditions.

While the oil thus passes down the plate stacks, superheated steam is generally admitted into the tower, normally through nozzle 2. As will be seen from FIG. 1, this nozzle is attached to an inner sparger which diverts the steam downwardly and thus equalizes the flow of the steam before it rises upwardly into the horizontal plates.

Also shown in FIG. 1 are several other nozzles, 2a and 2b. Under certain conditions of operation, particularly where difficult deodorizations or fatty acid stripping is required, it may be desirable to introduce the steam in stages through the various nozzles as shown. Although only three nozzles are shown serving three separate plate stacks, a typical plant may, of course, have many more of such nozzles, the number depending on the severity of the service required and the partial pressure buildup of the components to be removed from the oil.

As will be seen from this description, the ascending steam contacts the downward flowing liquid countercurrently. However, the steam passes over the liquid film on the horizontal plates, boils out the volatile matters responsible for the odors as well as the free fatty acids or glycerine, mixes with them and as mixed vapors sweeps them upwardly through the liquid distributor, then through another stack of generally three to five horizontal trays 9 that will remove from the vapor any entrained oil droplets that it may contain. As will be seen in contrast to horizontal plates 6, the horizontal plates 9 are not attached to the column shell 40. Hence there is actually a clearance 9a between these horizontal plates and the inside shell surface. As the droplet-laden vapor passes upwardly through horizontal plates 9, the droplets are deposited on the underside of the horizontal tray above. The liquid droplets will coalesce into larger drops and run along the underside to the edge of the plates 9, where they make contact with the inside column shell and are returned downwardly to the liquid distributor and hence the horizontal contacting plates 6. In order to facilitate this running over of the drops to the inside column, it is actually desirable to arrange the entrainment separation plates in the tower very slightly slanted. This is contrary to the horizontal contacting plates 6 which require that they be generally arranged in a reasonably horizontal position.

After an oil is properly deodorized, it must be cooled before it can be re-exposed to the atmosphere, because deodorized oil which is exposed to the air while still hot will tend to deteriorate and may reform odoriferous substances. In general, oils are rendered stable towards such degradation if they are cooled below about 150°F. in the total absence of air.

The cooling of the oil is in most instances done by pumping the oil out of the base of the deodorizing chamber through outside heat exchangers. Since in the deodorizer, and hence also still in the pump, the oil is generally under a high vacuum, there exists the constant danger that air will leak through the pump stuffing boxes into the oil and cause deterioration before effective cooling can be achieved and the oil thus safeguarded against this danger.

Now there are known ways by which the oil is cooled while it is still in the base of the deodorizer. Generally this is done by allowing the oil to form a deep pool, usually several feet deep, into which cooling coils are placed. The oil is held in this reservoir for a certain length of time to permit it to cool and it is then pumped out to storage. This method has obvious disadvantages. Firstly, due to the generally deep liquid pool and dependence on natural convection in a relatively high viscous fluid, the rates of heat transfer are very slow and cooling is tedious. Secondly, due to the large liquid hold-up, the method lacks flexibility and makes changeovers from one stack of oil to another difficult. Next due to the difficulty of purging the equipment properly, in a reasonable time after it has housed such a large hold-up of oil, contaminations are unavoidable. Finally due to the fact that the relatively cool liquid pool is at its upper boundary in contact with the superheated steam that enters just above for the deodorization, there will be a certain amount of cooling of the steam and there may even be condensation on the surface of the colder liquid pool in the base. This clearly is an uneconomical situation which should be avoided if at all possible.

The present invention embodies, in the lower section 39 of the deodorizer chamber, a novel feature which overcomes all of the aforementioned disadvantages. As will be seen, section 39 is separated from the upper section 37 by flanges 38 which hold in place the separating partition 22. This separating partition is, in essence, a flat trough, dished slightly downwardly so that it can accomodate a thin liquid pool 23 of perhaps an inch depth or so. On the lower side of the separating partition are attached pipe traps 24 that open into the thin shallow liquid pool above. As liquid drops from above into the liquid pool, it will fill the traps 24. Since the lower section 39 is essentially evacuated to the same pressure as the upper section 37, by connecting section 39 through nozzle 25 to the vacuum system, the traps 24 will deliver the liquid by gravity from the upper section 37 to the lower section 39, and the liquid once in the lower section, is wholly removed and separated from the steam entering at 2.

As the oil exits from traps 24, it will fill the liquid distributor plate 26, which has short feed nipples on its lower bottom side that are placed exactly over cooling pipe coils 27, that are connected to headers 29 to permit cooling water to enter through pipe 30 and leave through pipe 31 and pass through the coils. Instead of cooling coils, a special construction flat horizontal plate 28 may be used that is made of essentially the same horizontal plates as shown above 6 and 9, but where two plates have been welded together to form a flow chamber for carrying cooling water. After the oil has thus been cooled, it is safely pumped at B through outlet pipe 5 to storage.

It will be noted that by this arrangement all the inherent disadvantages of the conventional method of cooling have been eliminated. By virtue of using the separating partition 22, the entering hot steam is separated from the cooler liquid in the bottom and no steam is wasted. Furthermore, by letting the oil drop over the cooling coils, there is no oil hold-up and no time lag in case of changing stock. The rate of heat transfer is rapid because the oil flows over the cooling surface as a thin film. Finally, the equipment will drain clean in a minimum of time and will not lead to contamination.

The quality of a deodorized oil is generally judged by the observed flavor grade. Numerical values ranging from 1 to 10 are normally assigned to the flavor grades. An oil of best flavor would approach flavor grade 10. Oils of flavor grades 7.5 to 8.5 are generally quite acceptable. Whereas oils of less than 7.0 would require additional refining to meet general consumption standards.

In fatty acid stripping, the resulting oils can be tested very accurately for fatty acid content by the standard chemical methods. A typical oil requiring fatty acid stripping may initially contain as much as 8 to 10 percent of free fatty acid. Generally it is required to produce an oil of less than 0.1 percent fatty acid.

Frequently the deodorization may be achieved along with the fatty acid stripping, although there may be cases where the fatty acid removal must preceed the deodorization. In a typical deodorization, the oil would enter the top of the deodorizer chamber at 450°–490°F.. The ascending steam is essentially of the same temperature or perhaps 30° to 40°F. cooler.

There is an approximate upper limit of temperature for conducting the deodorization. Thus, generally speaking, it is advisable to remain below 575° to 600°F. as otherwise damage to the oil may occur.

The more precise temperatures of the oil and steam to be used in the deodorizer chamber depends, of course, also on the pressure. Generally speaking this may vary for the horizontal plate equipment from 1 to 50 millimeters in the top of the column with a most frequently used range of 3 to 10 millimeters.

For fatty acid stripping, the temperature situation is generally similar to that in deodorization. However, whereas in deodorization the amount of deodorizing steam used may be only equal to 1 to 2 percent, by weight, of the oil or less, — with fatty acid stripping the steam consumption is generally of the order of magnitude of 3 to 5 percent, or occassionally higher. The exact steam requirement for the steam stripping can be accurately calculated by applying the usual chemical engineering principles. Suffice to say that the steam requirement will depend chiefly on such factors as the extent of fatty acid removal desired, the operating pressure, the vapor pressures of the fatty acids to be removed, the operating temperature and, of course, the number of horizontal contacting plates that are used.

The number of horizontal plates for deodorization and fatty acid stripping may vary from a minimum of perhaps 10 plates for very simple cases to perhaps 200 plates or more for very difficult combinations of fatty acid stripping and deodorization. For most cases of deodorization or fatty acid stripping, between 50 to 100 horizontal plates will give acceptable results.

The height of such a plate arrangement accomodating perhaps 50 to 100 horizontal contacting plates, and bearing in mind the various loadings by oil and steam and the resulting pressure drops that can be tolerated, is between about 3 and 15 feet with the average usually employed being about 8 feet. This is very much lower than the height required for semicontinuous equipment or for packed towers where normally heights in excess of 20 to 25 feet are needed for similar duties.

The typical oil hold-up, for example, for a 75 horizontal plate unit having an oil film thickness of 0.35 millimeter will on a square foot basis be equal to $$\left(1 \times \frac{0.35}{25.4 \times 12}\right) \times 75 = 0.086 \text{ cubic feet.}$$

With a liquid density of, for example, 57 pounds per cubic foot this will be only $0.086 \times 57 = 4.9$ pounds.

In a comparable packed tower carrying 20 feet of 1-inch Pall rings, the hold-up is about 0.075 cubic foot of oil per cubic foot of packing, and the total hold-up will be equal to $0.075 \times 20 = 1.5$ cubic feet or $1.5 \times 57 = 85.5$ pounds.

It will be noted that this will be more than 17 times as much as with the horizontal plates. For the semi-continuous equipment referred to earlier, the hold-up would be even higher.

The residence times or contact times of the oil flowing through the horizontal plate tower is similarly very much shorter than through the other units. Thus for the semi-continuous unit, the contact time is of the order of magnitude of 1 to 2 hours, which reduce to perhaps 10 minutes for the packed tower. In the horizontal plate tower, on the other hand, the contact time will be of the order of magnitude of about a minute only.

Typical liquid loadings for deodorization as well as fatty acid and glycerine stripping that may be applied to the horizontal plate towers vary roughly from as low as 2 to perhaps 500 pounds of oil per hour per chimney in the plates. The preferred range of loading is, however, between 5 and 250 pounds per chimney per hour. The steam flows are normally such that the towers operate usually at pressure drops of about 0.05 to 5.0 millimeters of water per contacting plate, the preferred range of pressure drop per contacting plate being between 0.10 to 3.0 millimeters of water.

For some applications, the heated oil need not be passed through a flash chamber, such as 12, but may be introduced directly into the deodorizing chamber 1, either with or without the lower cooling section.

Thus it will be seen that I have provided a highly efficient apparatus and method for removing objectional odors or flavors from oils and fats, which apparatus is extremely compact and of such construction as to greatly minimize liquid hold-up, therefore greatly decreasing the production time and expense.

While I have illustrated and described a single specific embodiment of my invention, it will be understood that this is by way of illustration only, and that various changes and modifications may be contemplated in my invention and within the scope of the following claims.

I claim:

1. Apparatus for stripping volatile materials, such as fatty acids and glycerine, and for removing objectionable odors or flavors from oils and fats, comprising, a chamber enclosing a plurality of vertically stacked, parallely disposed, horizontally extending plates, means for introducing relatively oxygen-free heated oil at the top of said plates, each plate having a plurality of apertures wherein the distance between said apertures is less than the maximum width of said apertures, chimneys extending only downwardly from the perimeters of said apertures, the top surfaces of said plates being devoid of upwardly extending projections, said apertures being devoid of obstructions, whereby thin films of heated oil are formed on said plates, means for introducing superheated steam in the lower portion of said chamber so as to rise through said chimneys and apertures counter-currently of said oil and flow over said films of heated oil to boil out fatty acids and volatile odor-forming matter, and means for evacuating said fatty acids and odor-forming matter from the upper portion of said chamber.

2. Apparatus as recited in claim 1 wherein said apertures are circular.

3. Apparatus as recited in claim 1 wherein said chimneys are frusto-conically shaped, tapering downwardly and outwardly from said plates and being integral therewith.

4. Apparatus as recited in claim 1 wherein said first mentioned means comprises a flash chamber at subatmospheric pressure into which heated oil is passed before introduction into said stripping and deodorizing chamber, said flash chamber comprising vertically stacked horizontal plate means having a plurality of downwardly depending chimneys means through which said heated oil flows downwardly, means for introducing an inert gas into the bottom portion of said flash chamber and over films of said oil on said horizontal plate means to release oxygen from said oil, and means for evacuating said oxygen from said flash chamber.

5. Apparatus as recited in claim 2 wherein said apertures are at least 0.5 inch in diameter and not greater 6. Apparatus as recited in claim 4 wherein said plates in said flash chamber are vertically spaced apart between 0.25 to 6 inches and have diameters of between 0.25 and 4 inches.

7. Apparatus as recited in claim 1 in combination with a partition extending across an intermediate portion of said chamber and including means for allowing the oil to slowly flow therethrough but continuously maintain a reserve film of oil on said partition, thereby forming oil sealed upper and lower sections of said chamber of substantially the same pressure and through which partition stripped and deodorized oil flows downwardly, cooling means in said lower section onto which said stripped and deodorized oil will flow, and means for conducting cooled deodorized oil from said lower section.

8. Apparatus as recited in claim 7 wherein said means for allowing oil to flow slowly through said partition comprises trap means depending from said partition.

9. Apparatus as recited in claim 7 wherein said cooling means comprises coils through which cooling fluid is circulated and onto which coils said stripped and deodorized oil is deposited and forms a thin oil film before falling to the bottom portion of said chamber to provide a rapid rate of heat transfer.

* * * * *